United States Patent [19]

Malpass et al.

[11] Patent Number: 4,774,214
[45] Date of Patent: Sep. 27, 1988

[54] FLUOROALKOXYALUMINUM COMPOUNDS AND THEIR USE IN POLYMERIZATION PROCESSES

[75] Inventors: Dennis B. Malpass, La Porte; Andrzej M. Piotrowski, Houston; Michael J. Breen, La Porte, all of Tex.

[73] Assignee: Texas Alkyls, Inc., Deer Park, Tex.

[21] Appl. No.: 139,537

[22] Filed: Dec. 30, 1987

Related U.S. Application Data

[62] Division of Ser. No. 933,410, Nov. 21, 1986, Pat. No. 4,732,993.

[51] Int. Cl.$^4$ .............. B01J 31/38; B01J 21/00; C08F 4/64
[52] U.S. Cl. .................. 502/103; 502/169; 502/171
[58] Field of Search .............. 502/103, 169, 171; 556/181, 182

[56] References Cited

U.S. PATENT DOCUMENTS

| | | | |
|---|---|---|---|
| 3,442,082 | 1/1969 | Vandenberg | 502/103 X |
| 3,445,443 | 5/1969 | Sasaki et al. | 502/103 X |
| 3,485,770 | 12/1969 | Borchert et al. | 502/103 X |
| 3,661,878 | 5/1972 | Aishima et al. | 502/103 X |
| 4,547,473 | 10/1985 | Hamilton et al. | 502/103 X |
| 4,591,577 | 5/1986 | Sato et al. | 502/103 X |

Primary Examiner—Patrick P. Garvin
Assistant Examiner—George R. Fourson
Attorney, Agent, or Firm—Richard P. Fennelly; Louis A. Morris

[57] ABSTRACT

Novel compounds having the formula $$R_n Al(OR_f)_{3-n}$$

in which R is a $C_1$–$C_6$ alkyl group, $R_f$ is a $C_1$–$C_6$ fluoroalkyl group, and $0 \leq n < 3$ have been found suitable as Ziegler-Natta type co-catalyst components for polymerization or co-polymerization of olefins.

18 Claims, No Drawings

FLUOROALKOXYALUMINUM COMPOUNDS AND THEIR USE IN POLYMERIZATION PROCESSES

This is a division of application Ser. No. 933,410, filed Nov. 21, 1986, now U.S. Pat. No. 4,732,993.

This invention pertains to a series of novel fluoroalkoxyaluminum compounds which have been found useful as Ziegler-Natta catalyst components, particularly for high density polyethylene and polypropylene production.

The compounds of this invention have the general formula $$R_nAl(OR_f)_{3-n}$$

in which R is a $C_1$–$C_6$ alkyl group, $R_f$ is a $C_1$–$C_6$ fluoroalkyl group and $0 \leq n < 3$.

The term "alkyl" includes both straight and branched chain saturated hydrocarbyl groups of the aliphatic type. The term "fluoroalkyl" includes such an alkyl group substituted by one or more fluorine atoms. Preferably the fluoroalkyl group $R_f$ is a $C_2$–$C_4$ alkyl group substituted by at least three fluorine atoms; most preferably the terminal carbon atom (or atoms, if the alkyl group is terminally branched) is (are) substituted by three fluorine atoms.

Examples of such fluoroalkyl groups are 2,2,2-trifluoroethyl, 1-(trifluoromethyl)-2,2,2-trifluoroethyl and 2,2,3,3,4,4,4-heptafluorobutyl.

The value of n ranges from less than 3 to 0. Preferably, but not necessarily, n is 0, 1 or 2; however, the value of n need not be an integer.

As opposed to several fluoroalkylaluminum compounds described in the literature, the fluoroalkoxyaluminum compounds of the present invention are generally stable, mobile, and readily preparable in high yields.

The compounds of this invention may be prepared conveniently by one or more procedures. Dialkylaluminum fluoroalkoxide compounds (n=2) are readily prepared by reaction of the appropriate fluoroalkanol with a trialkylaluminum:

$$R_fOH + R_3Al \rightarrow R_2AlOR_f + RH$$

in which R and $R_f$ are as defined previously.

The reaction conditions will depend on the particular reactants employed. For instance, 2,2,2-trifluoroethanol reacts vigorously with triethylaluminum at the beginning of the procedure, though much slower at the end. In order to prevent a runaway reaction due to a buildup of unreacted trifluoroethanol, the trifluoroethanol should be added slowly to well stirred triethylaluminum with the temperature initially at 10° C. The temperature then is raised slowly to about 40° C. by slowly increasing the rate of addition of trifluoroethanol.

Alkylaluminum difluoroalkoxides (n=1) and aluminum tri-fluoroalkoxides (n=0) may also be prepared by stepwise reaction of the monofluoroalkoxide compound with further fluoroalkanol, for instance $$R_2AlOR_f + R_fOH \rightarrow RAl(OR_f)_2 + RH$$

and $$RAl(OR_f)_2 + R_fOH \rightarrow (R_fO)_3Al + RH$$

These reactions are generally carried out at temperatures from about 20° to about 60° C., with the temperature of each reaction similarly controlled by controlling the rate of addition of the fluoroalkanol.

Fluoroalkoxyaluminum compounds according to this invention in which n is not an integer may be similarly prepared, varying the ratio of reactants. Mixed fluoroalkoxy aluminum compounds, i.e, those containing two or more different fluoroalkoxy groups, may be similarly prepared using different fluoroalkanols in each stage. Alkylaluminum difluoroalkoxides, aluminum trifluoroalkoxides, and fluoroalkoxy aluminum compounds in which n is not an integer may also be prepared in one stage, by using the appropriate ratio of fluoroalkanol to trialkylaluminum:

$$nR_fOH + R_3Al \rightarrow R_n(AlOR_f)_{3-n} + 3\text{-}nRH$$

Some compounds of the present invention may also be obtained by first producing the corresponding fluoroalkoxy lithium compound by reaction of a fluoroalkanol with an alkyl lithium, and then reacting the lithium fluoroalkoxide with a dialkylaluminum halide, e.g. chloride:

$$R_fOH + R_aLi \rightarrow R_fOLi + R_aH$$

$$R_fOLi + R_2AlX \rightarrow R_fOAlR_2 + LiX$$

in which $R_a$ is a lower alkyl group such as n-butyl and X is a halogen, preferably chlorine or bromine. The lithium halide produced precipitates and the desired dialkylaluminum fluoroalkoxide is readily recovered from the reaction products.

The following are representative compounds of the present invention:
diethylaluminum 2,2,2-trifluoroethoxide $(C_2H_5)_2AlOCH_2CF_3$
ethylaluminum di-(2,2,2-trifluoroethoxide) $C_2H_5Al(OCH_2CF_3)_2$
aluminum tri-(2,2,2-trifluoroethoxide) $Al(OCH_2CF_3)_3$
diethylaluminum 2,2,3,3,4,4,4-heptafluorobutoxide $(C_2H_5)_2AlOCH_2(CF_2)_2CF_3$
diethylaluminum 1-(trifluoromethyl)-2,2,2-trifluoroethoxide $(C_2H_5)_2AlOCH(CF_3)_2$
di-(n-butyl) aluminum 2,2,2-trifluoroethoxide (n-$C_4H_9)_2AlOCH_2CF_3$ The following represent illustrative examples of processes for preparing compounds of this invention.

EXAMPLE 1

Preparation of Diethyl Aluminum 2,2,2-Trifluoroethoxide

Under a nitrogen atmosphere 81.36 g (0.71 mole) of triethylaluminum was placed in a flask immersed in a chilled oil bath (−20° C.). In an addition funnel there was placed 77 g (0.77 mole) of 2,2,2-trifluoroethanol. Temperature of the reaction mixture was permitted to rise to 10° C., at which point addition of the trifluoroethanol commenced. The temperature was slowly raised by increasing the speed of addition and at the end of the addition of the alcohol was 40° C. The total time consumed was one hour.

The product was fractionally distilled and a fraction boiling at 75°–78° C./approximately 5 mmHg was collected. Total amount of the product was 105.09 g, 80% of theoretical yield. Analysis for aluminum showed 14.66% Al, which correlated well with the theoretical value (14.66%). The product was additionally characterized by proton magnetic resonance as having resonances consistent with the indicated formula. The product remaining in the pot after distillation (total of 17.00 g) was also analyzed; the aluminum content was found to be 14.54%. The total yield was thus determined to be 93% of theoretical.

EXAMPLE 2

Preparation of Ethylaluminum Di-(2,2,2-trifluoroethoxide)

In a flask were placed 10.27 g (55.75 mmoles) of the product of Example 1, under a nitrogen blanket. Then, 5.71 g (0.058 mole) of 2,2,2-trifluoroethanol was added dropwise. When the reaction mixture temperature reached 50° C., the flask was immersed in a chilled oil bath (0° C.) and the addition of fluoroalkanol was continued at a rate sufficient to maintain the temperature at 50°-55° C. After addition was completed, the reaction mixture was stirred for one hour at 55° C. The product was a viscous, colorless liquid. Analysis for aluminum showed 10.43% Al, which correlated well with the theoretical value of 10.58%.

EXAMPLE 3

Preparation of Aluminum Tri-(2,2,2-trifluoroethoxide)

In a flask, under a nitrogen blanket, were placed 7.43 g (0.29 mole) of the product of Example 2 and 50 ml methylene chloride. Then, 3.07 g (0.031 mole) of 2,2,2-trifluoroethanol was added in a way so as to maintain the temperature at about 40° C. After the addition was complete, the flask was placed in an oil bath at 60° C. and most of the methylene chloride was evaporated. The product was allowed to stand at the same temperature for one hour and the remainder of the solvent stripped off under vacuum. There was obtained 9.09 g (95% of theoretical yield) of a white crystalline solid. Analysis for aluminum showed 8.36% Al. The theoretical value was 8.33%.

EXAMPLE 4

Preparation of Diethylaluminum 2,2,3,3,4,4-Heptafluorobutoxide

This example illustrates the production of a compound according to this invention through a lithium intermediate. Such a process is useful in cases of low reactivity of the starting fluoroalkanol.

Under a nitrogen atmosphere, there were placed in a flask 50 ml hexane and 2.30 g (0.0115 mole) 4,4,4,3,3,2,2-heptafluorobutanol. The flask was submerged in a cold oil bath and maintained at a temperature of −20° C. Then 0.0115 mole n-butyl lithium dissolved in n-hexane was added, with vigorous stirring. The reaction mixture (which at that time was in the form of a white suspension) was then stirred for one-half hour at the same temperature (bath temperature −20° C.), slowly warmed up to room temperature and allowed to stand overnight with stirring. The mixture was again placed in a cold oil bath (−20° C.) and 1.38 g (0.0115 mole) diethylaluminum chloride was added over a period of 15 minutes. The reaction mixture was warmed up to room temperature over a period of one hour and then stirred for two additional hours. Solid lithium chloride was separated by centrifugation and the clear supernatant isolated. Solvent n-hexane was evaporated under vacuum and the product was purified by short path vacuum distillation. Content of the clear, colorless liquid was anlayzed and found to contain 9.15% Al as compared with the theoretical value of 9.50%. In addition, the product was characterized by proton magnetic resonance, having resonances consistent with the indicated formulation.

The compounds of the present invention have been found useful as components of Ziegler-Natta olefin polymerization catalyst systems, particularly for production of polyolefins such as polyethylene and polypropylene and copolymers, for instance copolymers of ethylene with butene-1, hexene-1, octene-1 or 4-methylpentene-1. Such catalyst systems typically comprise a supported titanium-containing catalyst and an aluminum-containing co-catalyst. When used as a catalyst component for production of polyethylene, the compounds of the present invention may be used as the sole aluminum-containing co-catalyst or in combination with another aluminum-containing co-catalyst, for instance, a trialkylaluminum compound such as tri-isobutylaluminum. When used in a mixture with another aluminum-containing catalyst component, the compounds of the present invention may be employed in an amount up to about 50 mole % of the overall aluminum-containing catalyst component.

For production of polypropylene, the compounds of this invention are used in combination with another aluminum-containing catalyst component. In such case, the compounds of the present invention may be present in up to 100 mole % of the total aluminum-containing catalyst component, most preferably 10–50% of the total aluminum-containing component. Note, however, that in selected cases, higher levels (above 50% of total aluminum) of compounds according to this invention may result in catalysts having diminished productivity.

The compounds of this invention may also be used in combination with magnesium-containing materials utilized as olefin polymerization co-catalysts.

The following represent examples of the use of compounds of this invention in catalyst compositions for production of polyethylene and polypropylene. In the tables below the following abbreviations have been used: FAA=fluoroalkoxyaluminum compound, i.e., a compound of the present invention; TEAL=triethylaluminum; TIBAL=tri-isobutylaluminum; Et=ethyl; Bu=butyl; MI=Melt Index (ASTM method D-1238, Condition E at 190° C., 2160 gram load. Expressed as grams per 10 minutes); MIR=Melt Index Ratio. (Expressed as the ratio of the high load melt index (HLMI) to the melt index. HLMI obtained under same conditions as MI except with 21,600 gram load, condition F.).

In accordance with the usual practice, the productivity in the following tables is expressed as grams of polymer obtained per gram of catalyst. The specific activity is expressed as $$\text{kg polymer} \cdot \text{gTi}^{-1} \cdot \text{atmC}_2\text{H}_4^{-1} \cdot \text{hr}^{-1}$$

EXAMPLE 5

Polymerization of Ethylene

Example 5 illustrates the slurry polymerization of ethylene in an n-hexane solvent employing a silica-supported titanium catalyst component prepared from magnesium chloride, tetrahydrofuran, titanium tetrachloride and dehydrated porous silica, according to Example 1a of U.S. Pat. No. 4,359,561 (column 14, lines 34-60). The catalyst component so prepared contained 1.00% by weight titanium.

The polymerizations were carried out in a 4-liter reactor containing 2 liters of hexane stirred at 800-1000 rpm. Unless otherwise indicated, ethylene polymerizations were carried out for 1 hour at 85±1° C. Reactants were added in the following order: triethylaluminum; diethylaluminum 2,2,2-trifluoroethoxide (FAA) (when used); titanium catalyst component (200 mg); hydrogen (40 psig); ethylene (150 psig). After one hour the reactor was vented, the product filtered and vacuum dried. The following Table 1 shows results obtained with the amount of triethylaluminum and FAA expressed as a molar ratio of aluminum:titanium.

TABLE 1

| | | Polymerization of ethylene | | | |
|---|---|---|---|---|---|
| RUN | TEAL Al/Ti | $CF_3CH_2OAlEt_2$ FAA/Ti | PRODUCTIVITY | SPECIFIC ACTIVITY | |
| 5A* | 50 | — | 570 | 10.1 | comparison |
| 5B* | 45 | 5 | 510 | 9.1 | invention |
| 5C* | 25 | 25 | 510 | 9.1 | invention |

*Average of duplicate polymerizations.

EXAMPLE 6

The polymerization procedure of Example 5 was followed, except that two independently prepared titanium-containing catalyst components (prepared as in Example 1) were employed. The catalyst components are indicated as B and C in the following table. They contained 1.05 and 1.25% titanium, respectively.

Runs 6B, 6C and 6H demonstrate the use of fluoroalkoxyaluminum compounds according to the present invention in combination with a trialkylaluminum co-catalyst. Runs 6D, 6E and 6H demonstrate the use of fluoroalkoxyaluminum compounds of the present invention as the sole aluminum-containing co-catalyst.

Run 6F was conducted as a comparison, using instead of a compound of the invention, the compound diethylaluminum ethoxide as the sole catalyst component. As can be seen from the table, this compound, which is structurally similar to the trifluoroethoxy compound of the invention (run 6E), was totally ineffective as an ethylene polymerization co-catalyst.

The relatively low melt index obtained using the compounds of the present invention, which as can be seen from Table 2 is comparable to that when employed using a conventional aluminum-containing co-catalyst such as triisobutylaluminum, indicates that the polyethylene products obtained thereby may be suitable for use as film resins.

TABLE 2

| | | | | | Polymerization of Ethylene | | | | | | |
|---|---|---|---|---|---|---|---|---|---|---|---|
| Run | Catalyst | Co-catalyst | Al/Ti | FAA | FAA/Ti | Prod. | Spec. Act. | Bulk Dens g/ml | MI | MIR | |
| 6A[a] | B | TIBAL | 110 | — | — | 1190 | 15.1 | 0.33 | 0.8 | 27 | comparison |
| 6B | B | TIBAL | 60 | $(CF_3)_2CHOAlEt_2$ | 50 | 1140 | 14.5 | 0.32 | 1.5 | 27 | invention |
| 6C[b] | B | TIBAL | 100 | $(CF_3)_2CHOAlEt_2$ | 10 | 1230 | 15.7 | 0.31 | 2.0 | 26 | invention |
| 6D[b] | B | — | — | $(CF_3)_2CHOAlEt_2$ | 90 | 1200 | 15.3 | 0.32 | 1.8 | 26 | invention |
| 6E[a] | B | — | — | $CF_3CH_2OAl(n-Bu)_2$ | 135 | 670 | 8.5 | 0.29 | 0.4 | 23 | invention |
| 6F | B | — | — | $EtOAlEt_2$ | 90 | 0 | 0 | — | — | — | comparison |
| 6G[c] | C | TIBAL | 100 | — | — | 800 | 9.8 | 0.28 | 1.0 | 32 | comparison |
| 6H | C | TIBAL | 60 | $(CF_3)_2CHOAlEt_2$ | 40 | 820 | 10.0 | 0.28 | 0.4 | 44 | invention |
| 6I | C | — | — | $(CF_3)_2CHOAlEt_2$ | 110 | 1020 | 11.8 | 0.28 | 0.6 | 32 | invention |

[a]Average of duplicate polymerizations.
[b]Temperature range was 86.5 ± 2.5° C.
[c]Average of 8 polymerizations

EXAMPLE 7

This example demonstrates the utilization of the present compounds as aluminum-containing co-catalysts in the polymerization of propylene.

Slurry polymerization of propylene was carried out in a solvent (n-hexane) employing a magnesium-containing catalyst component (indicated as catalyst D) prepared according to Example 2 of U.S. Pat. No. 4,552,859.

Polymerization was carried out in a 4.5 liter reactor containing 2 liters hexane stirred at 600 rpm. The time of polymerization was 1.5 hours, the temperature was 65° C. Reactants were added in the following order: triethylaluminum; diethylaluminum 2,2,2-trifluoroethoxide (when used); methyl p-toluate (MPT) donor; catalyst component D (100 mg); hydrogen (3.2 psig); propylene (100 psig).

The reactor was vented after 1.5 hours, the product was filtered, washed and air dried. Table 3 shows the results obtained, with the quantity of triethylaluminum, fluroalkoxyaluminum, and MPT given in mmoles.

TABLE 3

| | | | Polymerization of Propylene | | | | |
|---|---|---|---|---|---|---|---|
| Example | Catalyst | TEAL | $CF_3CH_2OAlEt_2$ | MPT | Productivity | Isotactic Index | |
| 7A[a] | D | 12.0 | — | 3.0 | 5200 | 89.7 | comparison |
| 7B[b] | D | 10.8 | 1.2 | 3.0 | 3800 | 93.2 | invention |

TABLE 3-continued

| | | | Polymerization of Propylene | | | | |
|---|---|---|---|---|---|---|---|
| Example | Catalyst | TEAL | $CF_3CH_2OAlEt_2$ | MPT | Productivity | Isotactic Index | |
| 7C[b] | D | 6.0 | 6.0 | 3.0 | 1400 | 95.2 | invention |

[a] Average of four polymerizations.
[b] Average of duplicate polymerizations.

As can be seen from this table, the utilization of a fluoroalkoxyaluminum compound of the present invention produces polypropylene having a higher isotactic index than with triethylaluminum alone.

We claim:

1. A supported olefin polymerization catalytic system comprising a titanium halide catalyst and an aluminum-containing co-catalyst in which the co-catalyst comprises a compound having the formula $$R_nAl(OR_f)_{3-n}$$

in which R is a $C_1$-$C_6$ alkyl group, $R_f$ is a $C_1$-$C_6$ fluoroalkyl group, and $0 \leq n < 3$.

2. A catalytic system as claimed in claim 1 wherein the co-catalyst comprises a second organo-aluminum compound.

3. A catalytic system as claimed in claim 1 wherein the co-catalyst consists essentially of the compound.

4. A system according to any one of claims 1-3 in which R is a $C_1$-$C_4$ alkyl group.

5. A system according to any one of claims 1-3 in which $R_f$ is a $C_2$-$C_4$ fluoroalkyl group.

6. A system according to any one of claims 1-3 in which n is 2.

7. A system according to any one of claims 1-3 in which n is 1.

8. A system according to any one of claims 1-3 in which n is 0.

9. A system according to any one of claims 1-3 in which R is ethyl.

10. A system according to any one of claims 1-3 in which R is n-butyl.

11. A system according to any one of claims 1-3 in which $R_f$ is 2,2,2-trifluoroethyl.

12. A system according to any one of claims 1-3 in which $R_f$ is 1-(trifluoromethyl)-2,2,2-trifluoroethyl.

13. A system according to any one of claims 1-3 in which R is ethyl, $R_f$ is 2,2,2-trifluoroethyl, and n is 2.

14. A system according to any one of claims 1-3 in which R is ethyl, $R_f$ is 2,2,2-trifluoroethyl, and n is 1.

15. A system according to any one of claims 1-3 in which $R_f$ is 2,2,2-trifluoroethyl and n is 0.

16. A system according to any one of claims 1-3 in which R is ethyl, $R_f$ is 2,2,3,3,4,4,4-heptafluorobutyl, and n is 2.

17. A system according to any one of claims 1-3 in which R is ethyl, $R_f$ is 1-(trifluoromethyl)-2,2,2-trifluoroethyl, and n is 2.

18. A system according to any one of claims 1-3 in which R is n-butyl, $R_f$ is 2,2,2-trifluoroethyl, and n is 2.

* * * * *